(12) United States Patent
Hashimoto et al.

(10) Patent No.: US 9,572,347 B2
(45) Date of Patent: Feb. 21, 2017

(54) METHOD FOR INACTIVATING A VIRUS

(75) Inventors: Kazuhito Hashimoto, Kanagawa (JP); Kayano Sunada, Kanagawa (JP); Masahiro Miyauchi, Kanagawa (JP); Xiaoqing Qiu, Fujian (CN); Yoshinobu Kubota, Kanagawa (JP); Hitoshi Ishiguro, Baltimore, MD (US); Ryuichi Nakano, Tokyo (JP); Jitsuo Kajioka, Tokyo (JP); Yanyan Yao, Shanghai (CN)

(73) Assignees: THE UNIVERSITY OF TOKYO, Tokyo (JP); KANAGAWA ACADEMY OF SCIENCE AND TECHNOLOGY, Kanagawa (JP)

( * ) Notice: Subject to any disclaimer, the term of this patent is extended or adjusted under 35 U.S.C. 154(b) by 689 days.

(21) Appl. No.: 13/994,406

(22) PCT Filed: Dec. 22, 2010

(86) PCT No.: PCT/JP2010/073087
§ 371 (c)(1),
(2), (4) Date: Sep. 9, 2013

(87) PCT Pub. No.: WO2011/078203
PCT Pub. Date: Jun. 30, 2011

(65) Prior Publication Data
US 2013/0344124 A1 Dec. 26, 2013

(30) Foreign Application Priority Data
Dec. 24, 2009 (JP) ................................ 2009-292258

(51) Int. Cl.
*A01N 59/20* (2006.01)
*A01N 59/16* (2006.01)
*A01N 25/26* (2006.01)

(52) U.S. Cl.
CPC ............... *A01N 59/20* (2013.01); *A01N 25/26* (2013.01); *A01N 59/16* (2013.01)

(58) Field of Classification Search
CPC ......... A01N 59/20; A01N 25/26; A01N 59/16
See application file for complete search history.

(56) References Cited

U.S. PATENT DOCUMENTS

| 5,409,686 | A | 4/1995 | Mrusek et al. |
|---|---|---|---|
| 6,645,531 | B1 | 11/2003 | Antelman |
| 7,364,756 | B2 | 4/2008 | Gabbay |
| 2003/0199018 | A1 | 10/2003 | Gabbay |
| 2004/0224005 | A1 | 11/2004 | Gabbay |
| 2004/0247653 | A1 | 12/2004 | Gabbay |
| 2004/0255548 | A1 | 12/2004 | Hong et al. |
| 2005/0048131 | A1 | 3/2005 | Gabbay |
| 2005/0049370 | A1 | 3/2005 | Gabbay |
| 2005/0123589 | A1 | 6/2005 | Gabbay |
| 2007/0184079 | A1 | 8/2007 | Gabbay |
| 2010/0040655 | A1 | 2/2010 | Ren et al. |
| 2013/0011458 | A1 | 1/2013 | Gabbay |
| 2014/0141073 | A1 | 5/2014 | Gabbay |

FOREIGN PATENT DOCUMENTS

| CN | 1427672 | 7/2003 |
|---|---|---|
| CN | 1600424 | 3/2005 |
| CN | 1649629 | 8/2005 |
| CN | 101322939 | 12/2005 |
| CN | 1856253 | 11/2006 |
| CN | 101322939 | 12/2008 |
| EP | 0355885 | 2/1990 |
| EP | 2 332 554 | 6/2011 |
| EP | 2 374 354 | 10/2011 |
| JP | 08-157315 | 6/1996 |
| JP | 8-229408 | 9/1996 |
| JP | 11-349423 | 12/1999 |
| JP | 2000-070673 | 3/2000 |
| JP | 2002-068915 | 3/2002 |
| JP | 2003-528975 | 9/2003 |
| JP | 2005-170797 | 6/2005 |
| JP | 2006-232729 | 9/2006 |
| JP | 2007-504291 | 3/2007 |
| JP | 2008-44869 | 2/2008 |
| JP | 2008-148726 | 7/2008 |
| JP | 2008-149312 | 7/2008 |
| JP | 2009-526828 | 7/2009 |
| JP | 2010-168578 | 8/2010 |
| JP | 2010-239897 | 10/2010 |
| JP | 2010-270079 | 12/2010 |
| WO | 96/39144 | 12/1996 |

(Continued)

OTHER PUBLICATIONS

CN101322939—Espace machine translation (2008).*
Office Action issued in CN Patent Application No. 201080070802.X mailed Sep. 18, 2014; along with an English Translation thereof.
Office Action issued in EP Patent Application No. 10 839 433 9 mailed Oct. 24, 2014; along with an English Translation thereof.
Office Action issued in TW Patent Application No. 099145794 mailed Aug. 20, 2014; along with an English Tranlsation thereof.
Korean Office Action with respect to Korean Application No. 10-2013-7018740, which was mailed on Feb. 5, 2015;along with an English translation.
Chinese Office Action with respect to Chinese Application No. 201080070802.X, which was mailed on Feb. 15, 2015; along with an English translation.
Japanese Office Action with respect to Application No. 2011-139022, which was mailed on Apr. 7, 2015; along with an English translation.

(Continued)

*Primary Examiner* — Sue Liu
*Assistant Examiner* — Thor Nielsen
(74) *Attorney, Agent, or Firm* — Greenblum & Bernstein, P.L.C.

(57) ABSTRACT

An agent for virus inactivation capable of exhibiting inactivation action based on structural destruction such as degradation and decomposition against viruses, which comprises a monovalent copper compound such as cuprous oxide, cuprous sulfide, cuprous iodide, and cuprous chloride as an active ingredient, and a virus inactivation material, which contains the agent for virus inactivation on a surface of a substrate and/or inside of the substrate.

13 Claims, 10 Drawing Sheets

(56) References Cited

FOREIGN PATENT DOCUMENTS

| WO | 00/04908 | 2/2000 |
|---|---|---|
| WO | 01/49303 | 7/2001 |
| WO | 03/086478 | 10/2003 |
| WO | 2005/020689 | 3/2005 |
| WO | 2007-093808 | 8/2007 |
| WO | 2008/045992 | 4/2008 |
| WO | 2010-073738 | 7/2010 |
| WO | 2011/049068 | 4/2011 |

OTHER PUBLICATIONS

Naomi Arimura et al. Summary of Annual Meeting of 2004, The Society for Biotechnology, Japan.
Kazuhito Hashimoto et al., Clean Technology, 2009, vol. 19, No. 6, pp. 1-5.
Office Action for Chinese Application No. 201080070802.X, which was mailed on Mar. 27, 2014 with English translation.
Extended European Search Report for EP Patent Application No. 10839433.9, which is dated May 27, 2014.
"2660: Cuprous Chloride," The Merck Index, 14$^{th}$ edition, Jan. 1, 2006, Merck & Co., Whitehouse Station, NJ, USA, XP05516452, ISBN:978-0-91-191000-1, p. 2668.
Huan Pang et al., "Morphology effect on antibacterial activity of cuprous oxide," Chemical Communications, No. 9, Jan. 1, 2009, p. 1076, XP055118585, ISSN:1359-7345, DOI: 10.1039/b816670f.
Borkow, G. et al., "Putting copper into action: copper-impregnated products with potent biocidal activities," FASEB Journal, Fed. of American Soc. for Experimental Biology, U.S. vol. FJ Express, Sep. 2, 2004, pp. 1-19, XP009146599, ISSN:0892-6638, DOI:10.1096/FJ.04-2029FJE.
Sumiko Sanuki et al., "Photocatalytic Preparation of Cuprous Oxide Crystals Using a $TiO_2$ Catalyst," Material Transactions, Jan. 1, 2002, pp. 3247-3253, XP055116608, retrieved from the internet:URL: https://www.jim.or.jp/journal/e/pdf3/43/12/3247.pdf, retrieved on May 7, 2014.
Yong-Gang Zhang et al., "In situ Fenton Reagent Generated from $TIO_2/Cu_2O$ Composite film: a new way to utilize $TiO_2$ under visible light irradiation," Environmental Science & Technology, vol. 41, No. 17, Sep. 1, 2007, pp. 6264-6269, XP055116610, ISSN:0013-936X, DOI: 10.1021/es070345i.
International Preliminary Report on Patentability for International Application No. PCT/JP2010/073087, mailed on Jul. 4, 2013, and an English translation thereof.
Progress in Medicinal Chemistry, "Antimicrobial Activity and Action of Silver," vol. 31, pp. 351-370, 1994.
"The Molecular Mechanisms of Copper and Silver ion Disinfection of Bacteria and Viruses," CRC Critical Review Environ. Cont, vol. 18, pp. 295-315, 1989.
"Metal-based formulations with high microbicidal activity," Appl. Environ. Microbiol., vol. 58, pp. 3157-3162, 1992.
"Virus Inactivation by Copper or Iron Ions Alone and in the Presence of Peroxide," Appl. Environ. Microbiol., vol. 59, pp. 4374-4376, 1993.
"Cupric and Ferric Ions inactivate HIV," AIDS Research and Human Retroviruses, vol. 12, pp. 333-336, 1996.
"Mechanism of Copper-Mediated Inactivation of Herpes Simplex Virus," Antimicrobial Agents and Chemotherapy, vol. 41, pp. 812-817, 1997.
"Photocatalytic Antimicrobial Activity of Thin Surface Films of $TiO_2$, CuO, and $TiO_2$/CuO dual layers on *Escherichia coli* and Bacteriophage T4," Appl. Microbiol. Biotechnol. vol. 79, pp. 127-133, 2008.
"Characterization of Copper Oxide Nanoparticles for Antimicrobial Applications," International J. of Antimicrobial Agents, vol. 33, 587-590, 2009.
"Morphology effect on Antibacterial Activity of Cuprous Oxide," Chem. Comm., pp. 1076-1078, 2009.
"Visible-light photocatalysts in Nitrogen-Doped Titanium Oxides," Science, pp. 269-271, 2001.
"Nitrogen-Concentration Dependence on Photocatalytic Activity of $TiO_{2-x}N_x$ Powders," J. Phys. Chem. B., vol. 107, pp. 5483-5486, 2003.
"Hydrophilicity on Carbon-doped $TiO_2$ Thin Films under Visible Light," Thin Solid Films, vol. 510, pp. 21-25, 2006.
"Design of All-Inorganic Molecular-Based Photocatalysts Sensitive to Visible Light: Ti(IV)-O-Ce(III) Bimetallic Assemblies on Mesoporous Silica," J. Am. Chem. Soc., vol. 129, pp. 9596-9597, 2007.
"Efficient Visible Light-Sensitive Photocatalysts: Grafting Cu(II) ions onto $TiO_2$ and $WO_3$ photocatalysts," Chem. Phys. Lett., 457,pp. 202-205, 2008.
"Visible Light-Sensitive Cu(II)-Grafted $TiO_2$ Photocatalysts: Activities and X-ray Absorption Fine Structure Analyses," J. Phys. Chem. C., 113, pp. 10761-10766, 2009.
"Conduction Band Energy Level Control of Titanium Dioxide: Toward an Efficient Visible-Light Sensitive Photocatalyst," J. Am. Chem. Soc., 132, pp. 6898-6899, 2010.
"Visible-Light Driven $Cu(II)-(Sr_{1-y}Na_y)(Ti_{1-x}Mo_x)O_3$ Photocatalysts Based on Conduction Band Control and Surface Ion Modification," J. Am. Chem. Soc., 132, pp. 15259-15267, 2010.
Proceedings of Photo Functionalized Materials Society, Photocatalysis, 28, p. 4, 2009.
International Search Report for International Application No. PCT/JP2010/073087, mailed on Jan. 25, 2011.
Office Action for Japanese Patent Application No. 2009-292258, mailed on Feb. 12, 2014; along with an English excerption thereof.
Taiwan Office Action for Application No. 099145794, dated Mar. 13, 2015, along with an English translation thereof.
European Patent Office (EPO) Office Action for Application No. 10 839 433.9-1454, dated Apr. 24, 2015.
Taiwanese Office Action issued with respect to application No. 099145794, mail date is Jun. 30, 2015.
Korean Office Action issued with respect to application No. 10-2013-7018740, mail date is Aug. 25, 2015.
European Office Action issued with respect to application No. 10839433.9, mail date is Nov. 27, 2015.
S Rahimnejad et al., "A Credible Role of Copper Oxide on Structure of Nanocrystalline Mesoporous Titanium Dioxide", Journal of the Iranian Chemical Society, vol. 5, No. 3, Sep. 2008, pp. 367-374.
Tae Woo Kim et al., "Unique phase transformation behavior and visible light photocatalytic activity of titanium oxide hybridized with copper oxide", Journal of Materials Chemistry, vol. 20, No. 16, Jan. 2010, pp. 3238.
Hiromi Yamashita et al., "Degradation of propanol diluted in water under visible light irradiation using metal ion-implanted titanium dioxide photocatalysts", Journal of Photochemistry and Photobiology, A. Chemistry, vol. 148, No. 1-3, May 2002, pp. 257-261.
Korean Office Action issued with respect to application No. 10-2013-7018740, mail date is Dec. 14, 2015.
European Office Action issued with respect to application No. 10839433.9, mail date Jul. 6, 2016.

\* cited by examiner

METHOD FOR INACTIVATING A VIRUS

TECHNICAL FIELD

The present invention relates to an agent for virus inactivation which exhibits inactivating action, such as degradation and decomposition, on viruses such as influenza viruses.

BACKGROUND ART

It is currently known that metal ions such as silver ion ($Ag^+$), zinc ion ($Zn^{2+}$) and divalent copper ion ($Cu^{2+}$) suppress proliferation of microorganisms, or germicidally act against microorganisms. There have been developed variety kinds of antimicrobial materials consisting of these metal ions carried on a substance such as zeolite and silica gel, antimicrobial materials consisting of a combination with titanium oxide having a photocatalytic action, and the like.

As for the antimicrobial action or antiviral action of divalent copper ion, there have been elucidated actions of changing structures of cell membranes and destroying functions of the same (Progress in Medicinal Chemistry, 31, pp. 351-370, 1994) and action of denaturing nucleic acids (CRC Critical Rev. Environ. Cont., 18, pp. 295-315, 1989), and as for the action of divalent copper ion against viruses, there are reports by Sangripanti et al. (Appl. Environ. Microbiol., 58, pp. 3157-3162, 1992; Appl. Environ. Microbiol., 59, pp. 4374-4376, 1993; AIDS Res. Hum. Retrovir., 12, pp. 333-336, 1996; Antimicrob. Agent Chemother., 41, pp. 812-817, 1997). It has also been reported that a material having a glass surface coated with a thin film of copper(II) oxide (CuO) or a thin film containing CuO together with titanium oxide ($TiO_2$) had phage inactivating actions in a T4 phage experimental system (virus inactivation model) (Appl. Microbiol. Biotechnol., 79, pp. 127-133, 2008).

Although almost no reports have so far been made as for antimicrobial action of monovalent copper compounds, it has been reported that the antibacterial activity (MBC) of the monovalent copper compound ($Cu_2O$) against bacteria such as methicillin-resistant *Staphylococcus aureus* (MRSA), *Escherichia coli*, and *Pseudomonas aeruginosa* is inferior to that of divalent copper compound (CuO) or metallic copper (Cu), and remarkably weaker than that of silver (Ag) (International Journal of Antimicrobial Agents, 33, pp. 587-590, 2009, especially p. 589, Table 1). Further, there is also a report about differences in antibacterial activities of cuprous oxide due to the crystal polymorphism thereof (Chem. Commun., pp. 1076-1078, 2009), and bacteriostatic actions (MIC) against *Bacillus bacteria, Staphylococcus aureus, Pseudomonas aeruginosa* and the like may differ depending on the crystalline forms. However, it has not been reported that antibacterial activity of a monovalent copper compound is especially stronger than that of a divalent copper compound.

As for the antiviral action of a monovalent copper compound, nanoparticles with a mean particle size up to about 500 nm having an antiviral action are disclosed in Japanese Patent Unexamined Publication (KOHYO) No. 2009-526828, and it is explained that the nanoparticles may contain $Cu_2O$ in the paragraph [0020] of the patent publication. However, the aforementioned patent publication does not explicitly disclose the antiviral action of $Cu_2O$ per se, and those skilled in the art cannot understand whether or not a monovalent copper compound has a virus inactivating action in view of the disclosure of the publication.

PRIOR ART REFERENCES

Patent Document

Patent document 1: Japanese Patent Unexamined Publication (KOHYO) No. 2009-526828

Non-Patent Documents

Non-patent document 1: Progress in Medicinal Chemistry, 31, pp. 351-370, 1994
Non-patent document 2: CRC Critical Rev. Environ. Cont., 18, pp. 295-315, 1989
Non-patent document 3: Appl. Environ. Microbiol., 58, pp. 3157-3162, 1992
Non-patent document 4: Appl. Environ. Microbiol., 59, pp. 4374-4376, 1993
Non-patent document 5: AIDS Res. Hum. Retrovir., 12, pp. 333-336, 1996
Non-patent document 6: Antimicrob. Agent Chemother., 41, pp. 812-817, 1997
Non-patent document 7: Appl. Microbiol. Biotechnol., 79, pp. 127-133, 2008
Non-patent document 8: International Journal of Antimicrobial Agents, 33, pp. 587-590, 2009
Non-patent document 9: Chem. Commun., pp. 1076-1078, 2009

SUMMARY OF THE INVENTION

Object to be Achieved by the Invention

An object of the present invention is to provide an agent for virus inactivation which can exhibit inactivation action against viruses on the basis of structural destruction, such as degradation and decomposition.

Means for Achieving the Object

The inventors of the present invention conducted various researches to achieve the aforementioned object. As a result, they found that monovalent copper compounds such as cuprous oxide ($Cu_2O$), cuprous sulfide ($Cu_2S$), cuprous iodide (CuI) and cuprous chloride (CuCl) have remarkably stronger inactivating action against viruses as compared with divalent copper compounds such as cupric oxide (CuO) and cupric sulfide (CuS). They also found that marked virus inactivating action was also successfully attained with a composition consisting of a combination of a photocatalytic substance such as titanium oxide or metal-supporting titanium oxide and a monovalent copper compound. The present invention was accomplished on the basis of the aforementioned findings.

The present invention thus provides an agent for virus inactivation comprising a monovalent copper compound as an active ingredient.

According to preferred embodiments of the present invention, there are provided the aforementioned agent for virus inactivation, wherein the monovalent copper compound consists of one or two or more kinds of compounds selected from the group consisting of cuprous oxide, cuprous sulfide, cuprous iodide, and cuprous chloride; and the aforementioned agent for virus inactivation, which contains cuprous oxide in the form of microparticles.

According to other preferred embodiments of the present invention, there are provided the aforementioned agent for virus inactivation, which comprises one or two or more kinds of photocatalytic substances together with one or two or more kinds of monovalent copper compounds; and the aforementioned agent for virus inactivation, wherein the photocatalytic substance is a visible light-responsive photocatalytic substance.

According to further preferred embodiments of the present invention, there are provided the aforementioned agent for virus inactivation, which is in the form of a composition containing a monovalent copper compound and a photocatalytic substance; and the aforementioned agent for virus inactivation, wherein the photocatalytic substance carries a mixture of a monovalent copper compound and a divalent copper compound on a surface thereof.

The present invention further provides a virus inactivation material, which comprises the aforementioned agent for virus inactivation on a surface and/or inside of a substrate. According to preferred embodiments of this invention, there are provided a coating agent containing the aforementioned agent for virus inactivation; a virus inactivation material comprising the aforementioned agent for virus inactivation immobilized on a surface of a substrate; a virus inactivation material obtainable by curing a dispersion comprising the aforementioned agent for virus inactivation dispersed in a resin; and the aforementioned virus inactivation material, wherein the resin is a natural resin or a synthetic resin.

As other aspects of the present invention, there are provided a method for inactivating a virus, which comprises the step of contacting the virus with a monovalent copper compound; and use of a monovalent copper compound for manufacture of the aforementioned agent for virus inactivation.

There is also provided a method for producing an agent for virus inactivation comprising a photocatalytic substance which carries a mixture containing a monovalent copper compound and a divalent copper compound on a surface thereof, which comprises the step of adding a reducing agent to a suspension containing a divalent copper compound and titanium oxide particles.

From further aspect of the present invention, there is provided a photocatalytic substance which carries a mixture containing a monovalent copper compound and a divalent copper compound on a surface thereof.

Effect of the Invention

The agent for virus inactivation provided by the present invention is characterized in that it can exhibit an inactivation action on the basis of structural destruction, such as degradation and decomposition, against various viruses such as influenza viruses, and it can also exhibit the inactivation action in a dark place as well as a bright place. The agent can also exhibit the inactivation action even under a dry state or in the presence of water or organic substances and the like. For example, by incorporating the agent in a coated film formed with a coating material, floor polish, or the like, viruses in a wide area can be efficiently inactivated, and by incorporating the agent in molded resin products such as plastic products, viruses can be locally inactivated. Furthermore, by applying the agent to an inside filter of an air cleaner, inside of a warehouse, inside of a refrigerator, or the like, the agent can exhibit the virus inactivation action even in the absence of visible light or ultraviolet radiation, and therefore the agent is useful.

MODES FOR CARRYING OUT THE INVENTION

Figure 1:
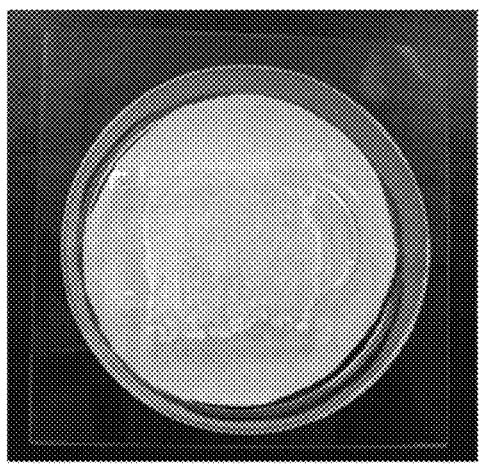
FIG. 1 is a conceptual diagram of the method for phage inactivation ability test (Examples 1 and 2).
Figure 1:
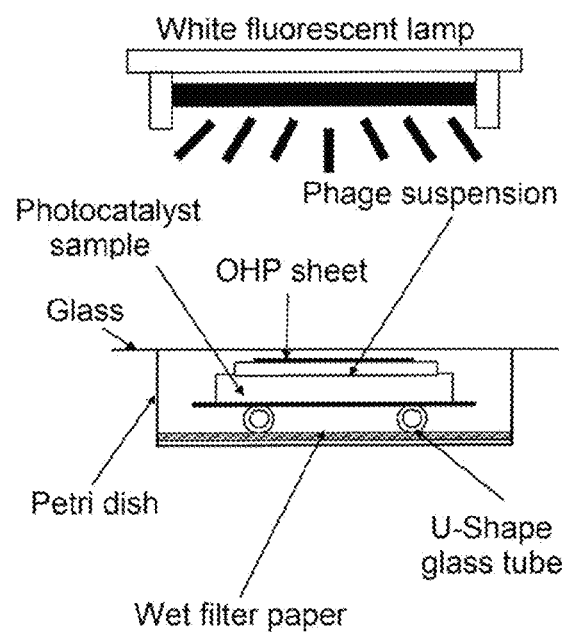

The term virus used in this specification means a DNA virus or an RNA virus, and further encompasses a bacteriophage that infects bacteria. Although objects to be applied with the agent for virus inactivation of the present invention are not particularly limited, examples include influenza virus, hepatitis virus, meningitis virus, human immunodeficiency virus (HIV), adult T cell leukemia virus, ebola disease virus, yellow fever virus, rabies virus, cytomegalovirus, severe acute respiratory syndrome (SARS) virus, chickenpox virus, rubella virus, poliovirus, measles virus, mumps virus, and the like. Preferred examples of the object include viruses that can spread by airborne infection, such as SARS virus and influenza virus. However, the objective viruses are not limited to these specific examples.

As the active ingredient of the agent for virus inactivation of the present invention, one or two or more kinds of monovalent copper compounds can be used. Although type of the monovalent copper compound is not particularly limited, examples include cuprous oxide ($Cu_2O$), cuprous sulfide ($Cu_2S$), cuprous iodide (CuI), cuprous chloride (CuCl), and the like.

As the agent for virus inactivation of the present invention, a monovalent copper compound of an arbitrary crystalline form having an arbitrary size can be used without any treatment. However, it is preferable to use a monovalent copper compound in a crystallized state prepared in the form of microparticles by an appropriate chemical process, a monovalent copper compound in the form of microparticle powder prepared by a mechanical grinding process, or the like. When a monovalent copper compound in the form of microparticles is used, the particle size of the microparticles is not particularly limited. For example, microparticles having a mean particle size of about 1 nm to 1,000 μm can be used. The minimum mean particle size is preferably about 100 nm or larger, more preferably about 200 nm or larger, still more preferably 500 nm or larger, most preferably 1 μm or larger. Although the maximum mean particle size is not particularly limited, it is preferably 800 μm or smaller, more preferably 500 μm or smaller. For example, when cuprous oxide ($Cu_2O$) is used, microparticles of different crystal forms can be prepared by using various conditions (Chem. Commun., pp. 1076-1078, 2009), and cuprous oxide of an arbitrary particle size and crystalline form can be used.

Further, the monovalent copper compound is not limited to a crystalline substance, and a substance of an arbitrary form, such as amorphous substance, mixture of crystals and amorphous substance at an arbitrary ratio, and microcrystalline substance of imperfect periodicity, can be used. Further, the monovalent copper compound may contain a small amount of a divalent copper compound, so long as the virus inactivation action is not inhibited. For example, it is also possible to use microparticles containing monovalent copper and divalent copper at an appropriate ratio, or the like as the monovalent copper compound. Therefore, the term "monovalent copper compound" used in this specification should not be construed in any limitative way, and should be construed in its broadest sense.

The agent for virus inactivation referred to in this specification can be used in a dark place, as well as in the presence of light such as infrared ray, visible light, and ultraviolet ray. The "dark place" referred to in this specification means a place where light does not substantially exist, more specifically, a place where any of visible light having a wavelength of about 400 to 800 nm, ultraviolet ray originating in sterilization lamp, sunlight, or the like (UV-C having a wavelength of 10 to 280 nm, UV-B having a wavelength of 280 to 315 nm, and UV-A having a wavelength of 315 to 400 nm), and infrared ray (wavelength of about 800 to 400,000 nm) does not substantially exist.

As the agent for virus inactivation of the present invention, for example, the agent for virus inactivation containing one or two or more kinds of monovalent copper compounds, and one or two or more kinds of photocatalytic substances can also be used. The term photocatalytic substance used in this specification means a substance that has a photocatalytic action, i.e., a substance having a light-induced decomposition action and/or a light-induced hydrophilization action for decomposing organic substances. As the photocatalytic substance, a substance having a superior light-induced decomposition action can be especially preferably used. As the photocatalytic substance, an ultraviolet responsive type photocatalytic substance, a visible light-responsive photocatalytic substance, and the like can be used. By using the agent for virus inactivation consisting of a combination of a monovalent copper compound and a photocatalytic substance as described above, virus inactivation action can be attained while light-induced decomposition action is exhibited in the presence of ultraviolet ray or visible light, and further, sufficient virus inactivation action can also be attained in a dark place.

When the agent for virus inactivation containing a monovalent copper compound and a photocatalytic substance is used as the agent for virus inactivation, ratio of the monovalent copper compound and the photocatalytic substance is not particularly limited. For example, the monovalent copper compound can be used within a ratio of about 0.1 to 95% based on mass of the photocatalytic substance. The composition can be generally prepared by mixing the monovalent copper compound and the photocatalytic substance at a predetermined ratio.

Hereafter, the photocatalytic substance that can be used in the agent for virus inactivation of the present invention in combination with the monovalent copper compound will be specifically explained. However, photocatalytic substances usable for the present invention are not limited to the following specific substances.

Among photocatalytic substances, ultraviolet responsive type photocatalytic substances are materials exhibiting a photocatalytic action in the presence of light containing ultraviolet radiation of 400 nm or shorter, and typically a titanium oxide photocatalyst can be used. The light-induced decomposition action of a titanium oxide photocatalyst is an action for inducing an oxidation-reduction reaction of electrons and positive holes, which are generated by excitation with ultraviolet radiation of 3.0 eV or higher and diffused on a surface, with molecules adsorbed on the surface.

Various titanium oxide photocatalysts having the light-induced decomposition action are known, and titanium oxide having an arbitrary crystalline structure, for example, anatase type, rutile type, brookite type, or the like, can be used. Titanium oxide of these types can be prepared by known methods such as the vapor phase oxidation method, sol-gel method, and hydrothermal method. Together with titanium oxide, one or two kinds of metals selected from, for example, the platinum group metals including platinum, palladium, rhodium, and ruthenium, can also be contained as a photocatalyst enhancer. Amount of the photocatalyst enhancer to be used is not particularly limited. For example, the photocatalyst enhancer can be used at a ratio of about 1 to 20% by weight based on the total amount of titanium oxide and the photocatalyst enhancer.

As visible light-responsive photocatalysts which exhibit photocatalytic activity in the presence of visible light such as indoor light, nitrogen-doped titanium oxide catalysts have recently been proposed (Science, 293, pp. 269-271, 2001; J. Phys. Chem. B, 107, pp. 5483-5486, 2003; Thin Solid Films, 510, pp. 21-25, 2006). Further, as visible light responsive photocatalysts of a structure different from those mentioned above, titanium oxide and tungstic oxide carrying nanoclusters of a copper compound and/or an iron compound have also been proposed (J. Am. Chem. Soc., 129, pp. 9596-9597, 2007; Chem. Phys. Lett., 457, pp. 202-205, 2008; J. Phys. Chem. C., 113, pp. 10761-10766, 2009; J. Am. Chem. Soc., 132, pp. 6898-6899, 2010; J. Am. Chem. Soc., 132, pp. 15259-15267, 2010). These visible light responsive type photocatalysts exhibit a photocatalytic activity in the presence of visible light containing light of, for example, 400 to 530 nm. These visible-light responsive photochatalytic materials can be used in the form of a composition obtained by mixing them with a monovalent copper compound. The visible-light responsive catalyst substance is not limited to the aforementioned specific catalysts.

More specifically, as the visible light responsive type photocatalytic substance, for example, a substance in the form of a composition containing a combination of (A) a copper compound and/or an iron compound and (B) at least one type of photocatalyst selected from the group consisting of tungstic oxide, titanium oxide, and titanium oxide of which conduction band is controlled by doping is preferred.

As the copper compound and iron compound which are used as the aforementioned component (A), a divalent copper salt and a trivalent iron salt, which allow easy electron transfer as a reduction catalyst of oxygen for the photocatalyst of the component (B), are preferred. Examples of the divalent copper salt and the trivalent iron salt include, for example, hydrogen halide salts (hydrogen fluoride salt, hydrogen chloride salt, hydrogen bromide salt, hydrogen iodide salt), acetate, sulfate, nitrate, and the like. As the component (A), one or more kinds of arbitrary compounds selected from the group consisting of copper compounds and iron compounds can be used, and it is preferable to make the photocatalyst of the component (B) carry the component (A) on the surface.

It is disclosed in Japanese Patent Unexamined Publication (KOKAI) No. 2008-149312 that a combination of tungstic oxide, which is the component (B), and a copper compound as a catalytic activity enhancer, which is the component (A), is useful as a visible light responsive type photocatalyst, and it is disclosed in Proceedings of Photo Functionalized Materials Society, Photocatalysis, 28, p. 4, 2009 that tungstic oxide carrying copper ions or iron ions is useful as a visible light responsive type photocatalyst. As a method for combining a copper compound and tungstic oxide, for example, there can be used a method of mixing 1 to 5 mass % of CuO powder with tungstic oxide powder, a method of adding a polar solvent solution containing a divalent copper salt (cupric chloride, cupric acetate, cupric sulfate, cupric nitrate and the like) to tungstic oxide powder to form a mixture, subjecting the mixture to a drying treatment, and then sintering the resultant at a temperature of about 500 to 600° C. to make the tungstic oxide surface carry copper ions, or the like. Amount of copper ions to be carried can be appropriately chosen in consideration of physical characteristics of the visible light responsive type photocatalyst and the like, and is not particularly limited.

For the preparation of a visible light responsive type photocatalyst using titanium oxide, it is preferable to combine titanium oxide with the component (A) to form, for example, copper-modified titanium oxide or iron-modified titanium oxide. Although the crystalline form of titanium oxide used as a raw material is not particularly limited, titanium oxide having a crystal structure of, for example, anatase type, rutile type, or brookite type, can be used.

As the copper ion species existing on the surface of the copper-modified titanium oxide, for example, copper ion species originating in copper(II) chloride, copper(II) acetate, copper(II) sulfate, copper(II) nitrate, copper(II) fluoride, copper(II) iodide, copper(II) bromide, and the like can be used, and copper ion species originating in copper(II) chloride can be preferably used. The copper ion species are generated by a chemical reaction such as decomposition or oxidization of a copper compound such as copper(II) chloride, or physicochemical change such as precipitation.

Amount of copper ion species in the modified titanium oxide is not particularly limited. For example, the amount may be 0.05 mass % or more, preferably 0.1 mass % or more, in terms of metallic copper (Cu) based on titanium oxide, from a viewpoint of improvement in performance of the photocatalyst, and may be 0.3 mass % or less from viewpoints of prevention of aggregation of the copper ion species and prevention of performance degradation of the photocatalyst.

The copper-modified titanium oxide can be prepared by, for example, the step of hydrolyzing a titanium compound which generates titanium oxide in a reaction solution, and the step of mixing an aqueous solution containing copper ion species with the solution after the hydrolysis to attain surface modification of the titanium oxide.

In the hydrolysis step, for example, a titanium chloride aqueous solution can be hydrolyzed to obtain a titanium oxide slurry, and an arbitrary crystalline form can be prepared by modifying conditions of the solution used for the hydrolysis. For example, titanium oxide particles having a brookite content of 7 to 60 mass %, or brookite crystals having a crystallite size of about 9 to 24 nm can be obtained. For example, the hydrolysis and aging can be performed in a temperature range of 60 to 101° C., a dropping velocity of 0.6 to 2.1 g/minute can be used for titanium tetrachloride aqueous solution, or the step of dropping 5 to 20 mass % of hydrochloric acid can be added, or a step can further be added which consists of an arbitrarily combination thereof.

By performing the surface modification step in a temperature range of, for example, 80 to 95° C., preferably 90 to 95° C., surface of titanium oxide be efficiently modified with copper ion species. The modification with copper ion species can be attained by, for example, the method described in Proceedings of Photo Functionalized Materials Society, Photocatalysis, 28, p. 4, 2009, specifically, a method of mixing photocatalyst particles and copper chloride in a solvent with heating, then washing the particles, and collecting the particles, a method of mixing photocatalyst particles and copper chloride in a solvent with heating, then evaporating the mixture to dryness, and collecting the particles, or the like.

The crystalline form of titanium oxide in the iron-modified titanium oxide may be any of anatase type, rutile type, and brookite type, and it may be an arbitrary mixture of titanium oxide of these types. In the case of the iron-modified titanium oxide, it is preferable to use titanium oxide of high crystallinity, namely, titanium oxide of low amorphous titanium oxide or titanium hydroxide content is preferred.

Titanium oxide of which conduction band is controlled by doping is titanium oxide doped with metal ions, wherein effect of shifting the lower end electric potential of the conduction band of the titanium oxide to the positive electric potential side can be expected, or metal ions wherein effect of forming an isolated level on the positive electric potential side of the lower end electric potential of the conduction band of the titanium oxide can be expected. Examples of the metal ions with which the aforementioned effects can be expected include, for example, those of tungsten(VI), gallium(III), cerium(IV), germanium(IV), barium(V), and the like, and two or more kinds thereof may be used in combination. Preferred examples of the titanium oxide of which conduction band is controlled by doping include, for example, tungsten-doped titanium oxide, tungsten-gallium co-doped titanium oxide, and the like. A mixture containing any of these types of doped titanium oxide in combination with the copper compound or iron compound as the component (A), or a visible light responsive type catalyst comprising doped titanium oxide carrying a divalent copper salt and/or a trivalent iron salt on the surface is preferred.

Form of titanium oxide to be doped is not particularly limited. For example, titanium oxide in the form of microparticles, titanium oxide in the form of thin film, and the like can be used. It is preferable to use titanium oxide in the form of microparticles, which has a large specific surface area. The crystalline structure of titanium oxide is not particularly limited, and rutile type, anatase type, brookite type crystals, or an arbitrary mixture thereof can be used. When the titanium oxide contains rutile type crystals as the main component, it preferably contains such crystals at a content of 50 mass % or higher, more preferably a content of 65 mass % or higher. The same shall apply to cases where anatase type or brookite type crystals are contained as the main component.

When tungsten is doped, the molar ratio of tungsten and titanium (W:Ti molar ratio) is preferably in the range of 0.01:1 to 0.1:1, more preferably in the range of 0.01:1 to 0.05:1, still more preferably in the range of 0.02:1 to 0.04:1. When tungsten and gallium are co-doped, it is ideal that the molar ratio of tungsten and gallium (W:Ga molar ratio) is close to 1:2, and the ratio is preferably at least in the range of 1:1.5 to 1:2.5, more preferably in the range of 1:1.7 to 1:2.3, still more preferably in the range of 1:1.8 to 1:2.2. Amount of the divalent copper salt or trivalent iron salt carried on the surface of the doped titanium oxide is about 0.0001 to 1 mass %, more preferably 0.01 to 0.3 mass %, on the basis of the total amount of the photocatalytic substance.

The visible light responsive type photocatalyst comprising doped titanium oxide carrying a divalent copper salt and/or a trivalent iron salt on the surface can be prepared with, for example, the doping step of obtaining tungsten-doped titanium oxide or tungsten-gallium co-doped titanium oxide, and the metal salt deposition step of making the titanium oxide carry the divalent copper salt and/or the trivalent iron salt.

The doping step may be performed by, for example, (1) a method of preparing doped titanium oxide according to the sol-gel method; (2) a method of preparing doped titanium oxide by mixing a solution containing a tetravalent titanium salt with a dopant solution heated to a predetermined temperature; (3) a method of preparing doped titanium oxide by mixing a gas containing volatile titanium compound vapor and volatile tungsten compound vapor or such a gas as mentioned above further containing volatile gallium compound vapor with a gas containing an oxidative gas according to the vapor-phase method; or a method of preparing doped titanium oxide by making titanium oxide powder carry a hexavalent tungsten salt or a hexavalent tungsten salt and an oxidized gallium salt on the surfaces, and sintering the powder at a temperature of about 800 to 1,000° C.

The step of making doped titanium oxide carry a divalent copper salt and/or a trivalent iron salt on the surface can be performed by a method for making the doped titanium oxide carry the divalent copper salt and/or the trivalent iron salt as thinly as possible so that the divalent copper salt and/or the trivalent iron salt can maintain a highly dispersed state in the form of microparticles on the surfaces of the doped titanium oxide. This step can be preferably performed by a method of contacting the doped titanium oxide and an aqueous solution of the divalent copper salt and/or the trivalent iron salt, heating them to a temperature of about 85 to 100° C., preferably about 90 to 98° C., then collecting solid by filtration, centrifugation or the like, and sufficiently washing the solid with water.

As the agent for virus inactivation of the present invention, the agent for virus inactivation in the form of a composition containing a monovalent copper compound and a photocatalytic substance may be used. Further, in order to simultaneously obtain both high antiviral effect and photocatalytic activity, the agent for virus inactivation comprising a photocatalytic substance can also be used wherein a mixture containing a monovalent copper compound and a divalent copper compound is carried on the surface thereof. In a preferred embodiment of the agent for virus inactivation comprising a photocatalytic substance that carries a mixture containing a monovalent copper compound and a divalent copper compound on the surface thereof, titanium oxide, more preferably particles of titanium oxide, can be used as the photocatalytic substance. Although particle size of the titanium oxide particles is not particularly limited, the particle size may be, for example, about 5 to 1,000 nm. In a preferred embodiment, nanoclusters of a mixture containing a monovalent copper oxide and a divalent copper oxide can be formed and carried on the photocatalytic substance, preferably surfaces of particles of the photocatalytic substance. The monovalent copper compound or the divalent copper compound contained in the mixture may be in a crystalline form, amorphous state, or a mixture of the compound in crystalline and amorphous states. It is preferred that both of the monovalent copper compound and the divalent copper compound are carried as amorphous substances on the surface of the photocatalytic substance.

Examples of the method for forming nanoclusters containing a mixture of monovalent copper oxide and divalent copper oxide carried on the surfaces of titanium oxide particles include, for example, a method comprising the step of adding a reducing agent to a suspension containing a divalent copper compound and titanium oxide particles. Preferred examples include a method comprising the step of preparing a suspension containing a divalent copper compound and titanium oxide particles, and adding a reducing agent under a basic condition, for example, after pH is adjusted to 9, or such a method as mentioned above, wherein temperature of the suspension is maintained to be 60° C. or higher. However, the method is not limited to these specific methods.

As the reducing agent, there can be used, for example, at least one kind of substance selected from the group consisting of an alkali metal, an alkaline earth metal, aluminum, zinc, amalgam of an alkali metal or zinc, hydride of boron or aluminum, a low oxidized metal salt, hydrogen sulfide, sulfide, thiosulfate, oxalic acid, formic acid, ascorbic acid, a substance having an aldehyde bond, an alcohol compound including phenol, and the like. A substance having an aldehyde bond can be preferably used as the reducing agent. As the substance having an aldehyde bond, for example, a saccharide, more preferably glucose, can be used. However, the agent is not limited to these examples. Saccharides are preferred reducing agents, since they are inexpensive, have no toxicity, and can be easily removed by a common operation such as washing after a reduction reaction. When the reaction is performed after the suspension containing a divalent copper compound and titanium oxide particles is made basic, pH can be generally controlled by using a metal hydroxide, for example, an alkali metal hydroxide such as sodium hydroxide, but the reaction condition is not limited to a basic condition.

The aforementioned preparation method will be more specifically explained below. However, the present invention is not limited by the following explanations. For example, titanium oxide particles carrying copper oxide ($Cu_xO$) nanoclusters on the surfaces can be prepared by preparing a suspension by suspending titanium oxide particles in an aqueous solution of a divalent copper compound such as $CuCl_2$ and stirring the mixture with warming at a temperature of, for example, 60° C. or higher, preferably at about 90° C., for several hours, preferably about 1 hour, to prepare a suspension, then adding sodium hydroxide (NaOH/$Cu^{2+}$=0 to 8) and a saccharide (for example, glucose or the like; aldehyde compound/$Cu^{2+}$=4) to the suspension, stirring the mixture under a condition of pH 9 or higher with further warming preferably at a temperature of 60° C. or higher, more preferably at about 90° C., for several hours, preferably about 1 hour, collecting the resulting solid by filtration, washing the solid with water, and drying the solid. The microparticles obtained by this reaction are composite particles carrying nanoclusters of $Cu_xO$ containing $Cu_2O$ generated by the reaction represented as R—CHO+2$Cu^{2+}$+4$OH^-$->R—COOH+$Cu_2O$+2$H_2O$ (mixture of monovalent and divalent copper oxides) as the main component on the surfaces of the $TiO_2$ particles, and they can be preferably used in the present invention as composite particles having both light-induced decomposition action and virus inactivation action.

Form of the agent for virus inactivation of the present invention for practical use is not particularly limited. For example, the agent for virus inactivation in a solid form such as impalpable powder or granules can be filled in an appropriate container and used without further treatment, or the agent for virus inactivation can be used in a form that it is contained on a surface and/or inside an arbitrary substrate, and the latter form is generally preferred. The "virus inactivation material" used in this specification means a material containing the aforementioned agent for virus inactivation on a surface and/or in inside of a substrate. Examples of the substrate include, for example, a substrate consisting of a single member of a common material such as metal, ceramics, or glass, and a composite substrate consisting of two or more kinds of members, but the substrate is not limited to these examples. Further, a material comprising a coating agent removable with an appropriate means such as floor polish and containing the aforementioned agent for virus inactivation also encompassed by the virus inactivation material of the present invention. Furthermore, composite particles consisting of titanium oxide particles carrying nanoclusters containing a mixture of a monovalent copper oxide and a divalent copper oxide on the surfaces can be immobilized on a continuous film to expose the nanoclusters containing a mixture of a monovalent copper oxide and a divalent copper oxide on a surface of the film. Alternatively, there can also be used the agent for virus inactivation in the form of a film in which the surface of titanium oxide in the form of a thin film, sputtered on glass, is sputtered with a thin film of nanoclusters containing a mixture of a monovalent copper oxide and a divalent copper oxide, or the like.

Examples of the virus inactivation material comprising a substrate having a surface, on which the agent for virus inactivation is immobilized, generally include a material comprising a substrate having a surface on which the agent for virus inactivation is immobilized by using an immobilization means such as a binder. As the binder, an organic type binder or an inorganic type binder may be used. When a composition containing a monovalent copper compound and a photocatalytic substance is used as the agent for virus inactivation, an inorganic type binder is preferably used to avoid decomposition of the binder by the photocatalytic substance. Type of the binder is not particularly limited, and an arbitrary binder, for example, an inorganic binder such as silica type binder usually used for immobilizing a photocatalytic substance on a substrate surface, a polymer binder that can form a thin film through polymerization or solvent evaporation, and the like can be used.

Examples of the virus inactivation material containing the agent for virus inactivation inside a substrate include a material obtainable by curing a dispersion comprising a resin in which the aforementioned agent for virus inactivation is dispersed. As the resin, a natural resin or a synthetic resin may be used. Examples of the resin include, for example, acrylic resin, phenol resin, polyurethane resin, acrylonitrile/styrene copolymer resin, acrylonitrile/butadiene/styrene copolymer (ABS) resin, polyester resin, epoxy resin, and the like, but the resin is not limited to these specific resins.

A mode of application of the agent for virus inactivation of the present invention is not particularly limited. The agent can be used in the presence of an arbitrary light, and the agent can also be used in a dark place. Further, the agent for virus inactivation of the present invention has high virus inactivation ability even in the presence of water (for example, in water, sea water, and the like), under a dry condition (for example, low humidity condition in winter and the like) or a high humidity condition, or in the presence of an organic substance, and accordingly the agent can persistently inactivate viruses. The agent can be applied to arbitrary objects, for example, wall, floor, and ceiling as well as buildings such as hospitals and factories, machining tools, measurement devices, inside and parts of electric appliances (insides of refrigerator, washing machine, dish washer, and the like, filter of air cleaner, and the like). Preferred examples of the dark place include inside of machines, storage room of refrigerator, and hospital facilities darken at night or at the time of unused (waiting room, operating room, and the like), but not limited to these examples. Further, air cleaner products incorporated with a ceramic filter coated with titanium oxide and a light source for irradiating the filter with ultraviolet radiation have been proposed as countermeasures against influenza, and if the agent for virus inactivation of the present invention is applied to such filter, the ultraviolet light source becomes unnecessary, thus cost can be reduced, and safety can be enhanced.

EXAMPLES

Hereafter, the present invention will be more specifically explained with reference to examples. However, the scope of the present invention is not limited to the following examples.

Example 1

The virus inactivation ability was mainly studied by the following method through model experiment using bacteriophages, although evaluation was also made for influenza viruses. A method of using the inactivation ability against bacteriophages as a model of virus inactivation ability is described in, for example, Appl. Microbiol. Biotechnol., 79, pp. 127-133, 2008, and it is known that such a method provides reliable results.

Filter paper was placed in a deep petri dish, and a small volume of sterilized water was added. A glass stand of about 5 mm was placed on the filter paper, and a glass plate applied with a test sample such as $Cu_2O$ was placed on the glass stand. A prepurified Qβ phage (NBRC 20012) suspension, of which concentration was also determined beforehand, was added dropwise in a volume of 50 μL onto the glass plate, and an OHP film was put thereon in order to have the surface of the material contact with the phages. This petri dish was covered with a glass plate. Similar measurement sets were prepared in a number of times of scheduled measurement of phage counts, and left standing in a dark place at room temperature. As a light source, a 15 W white fluorescent lamp (full white fluorescent lamp FL15N, Panasonic Corporation) provided with an ultraviolet cut off filter (KU-1000100, King Works Co., Ltd.) was used, and each measurement set was left standing at such a position that illumination was 800 luxes (measured with an illuminometer TOPCON IM-5). After a predetermined time passed, phage concentration of each sample was measured. A conceptual diagram of the measurement method is shown in FIG. 1.

The phage concentration was measured by the following method. Each sample was immersed in 10 mL of a recovery solution (SM buffer), and shaken for 10 minutes on a shaking machine. This phage recovery solution was appropriately diluted, and mixed with a culture medium of *Escherichia coli* (NBRC 13965) separately cultured ($0D_{600}>1.0$, $1×10^8$ CFU/mL), and the mixture was stirred, and left standing in an incubator at 37° C. for 10 minutes, so that *Escherichia coli* was infected with the phage. This mixture was inoculated on an agar medium, culture was performed at 37° C. for 15 hours, and then the number of phage plaques was visually counted. The resulting number of plaques was multiplied with the dilution times of the phage recovery solution to obtain the phage concentration.

Figure 7:
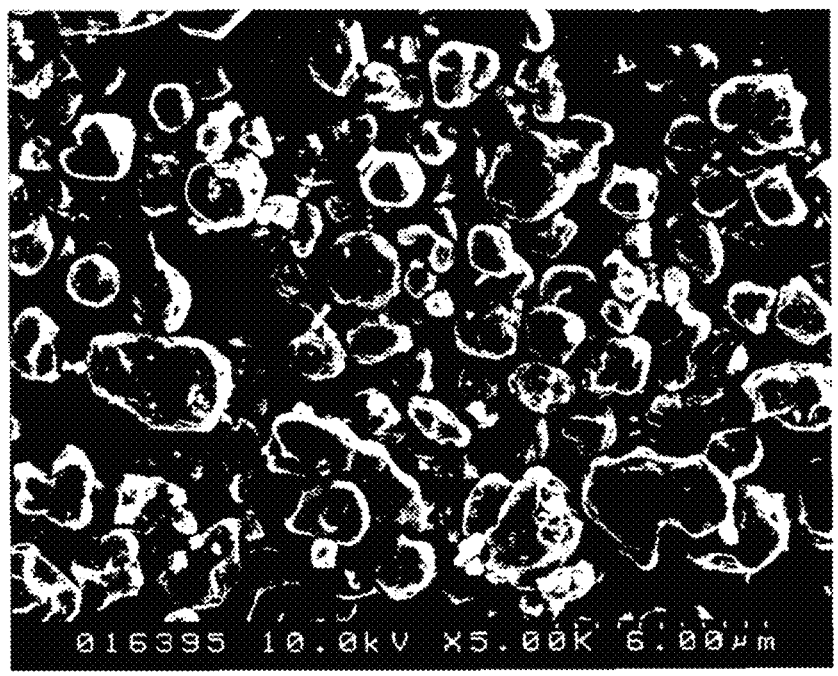
FIG. 7 is a scanning electron microscopic image of $Cu_2O$ powder used in Example 1.

$Cu_2O$ powder was subtilized in a mortar, and a 0.1 mass % ethanol slurry was prepared. Particle size of $Cu_2O$ was 1 to 4 μm as observed with a scanning electron microscope (SEM) (FIG. 7). When the slurry was prepared, the powder particles were dispersed by irradiating ultrasonic waves for 20 minutes with an ultrasonic washing machine. This dispersion was added dropwise onto whole surface of a glass plate of 2.5 cm×2.5 cm×1 mm (thickness) while avoiding overflow of the dispersion from the glass plate, and this glass plate was put into a constant temperature dryer set at 120° C., and dried for 3 hours. $Cu_2O$ was obtained on the glass plate in an amount of 0.15 mg/6.25 $cm^2$ (=0.24 $g/m^2$). A sample of CuO was prepared in the same manner, provided that the amount was adjusted to 0.17 mg/6.25 $cm^2$ (=0.27 $g/m^2$) so as to obtain the same copper ion ratio, and as for CuS, the amount was adjusted to 0.2 mg/6.25 $cm^2$ (=0.32 $g/m^2$). Similarly, the amount of $Cu_2S$ was adjusted to 0.17 mg/6.25 $cm^2$ (=0.27 $g/m^2$), and the amount of CuI was adjusted to 0.4 mg/6.25 $cm^2$ (=0.64 $g/m^2$). $Cu_2S$ had a particle size of several tens of micrometers due to aggregation after the pulverization.

Figure 2:
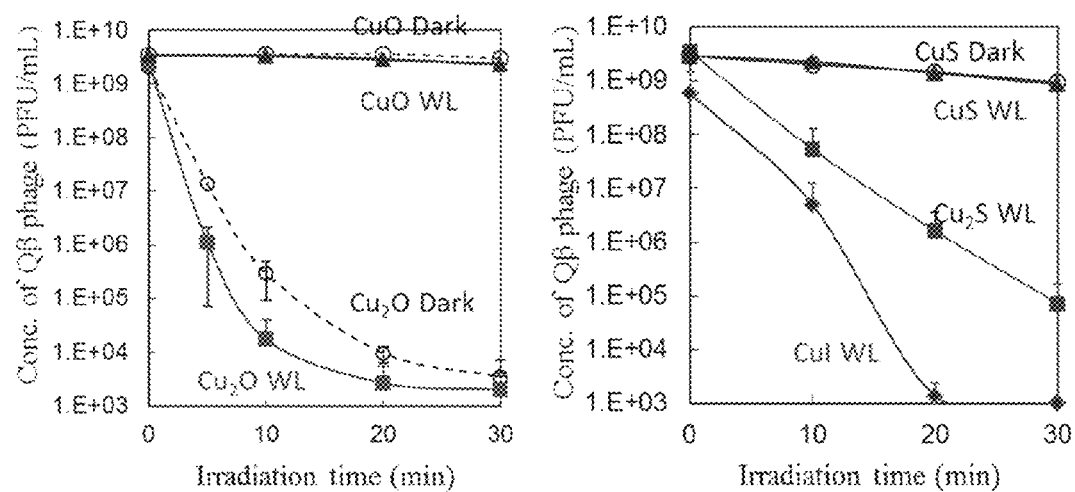
FIG. 2 shows the effect of the agent for virus inactivation of the present invention. In the figure, WL indicates the test results obtained under irradiation of white light, and Dark indicates the test results obtained in a dark place.

The results are shown in FIG. 2. When the phage suspension was contacted with $Cu_2O$ consisting of a monovalent copper compound for 30 minutes, the phage concentration decreased to $1/10^6$ of the initial concentration, whereas CuO consisting of a divalent copper compound gave almost no inactivation effect with contact of 30 minutes (left graph in FIG. 2). Further, the phage inactivation effect of $Cu_2O$ was observed both under light irradiation (WL, white light) and in the dark place (Dark). CuS consisting of a divalent copper compound also gave almost no inactivation effect, in the same manner as CuO (right graph in FIG. 2). Whilst, $Cu_2S$ and CuI consisting of a monovalent copper compound gave high phage inactivation effect in the same manner as $Cu_2O$, and it was revealed that a monovalent copper compound exhibited superior phage inactivation effect (right graph in FIG. 2). When phage inactivation ability of cuprous chloride (CuCl) was investigated in a similar manner, it was observed that the chloride had almost the same phage inactivation ability as that of cuprous oxide.

Example 2

Figure 3:
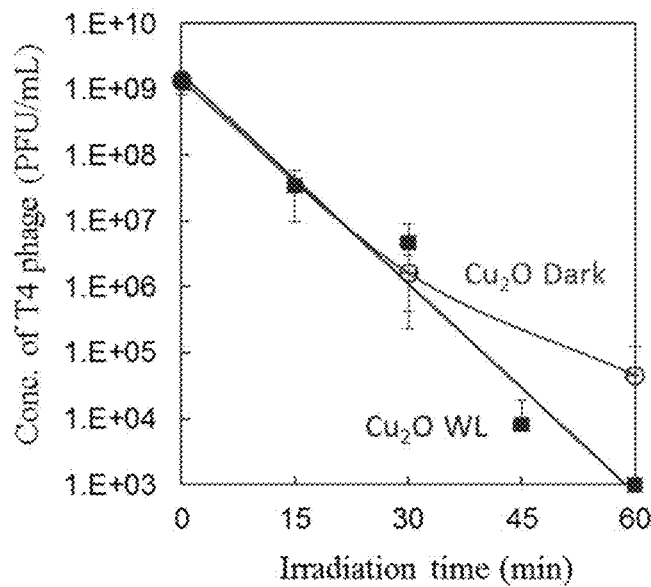
FIG. 3 shows the effect of the agent for virus inactivation of the present invention against T4 phage.

Virus inactivation action against T4 phage (NBRC 20004) was investigated in the same manner as that of Example 1. As a result, by contacting the phage with $Cu_2O$ for 60 minutes under irradiation of white fluorescence, concentration of the T4 phage was decreased to $1/10^6$ (FIG. 3).

Example 3

As influenza virus, A/PR/8/34 (H1N1) was used. A virus solution was inoculated to a 12th day embryonated chicken egg to establish infection, and the egg was incubated at 35.5° C. for two days. After the egg was left standing overnight at 4° C., chorioallantoic fluid was collected, and s concentrate thereof was obtained by precision filtration (removal of egg-derived contaminants) and ultrafiltration (removal of impurities, concentration of viruses). This concentrate was purified by sucrose density gradient sedimentation velocity method based on ultracentrifugation (linear gradient of 5 to 50% sucrose, 141,000×g, 3 hours) to obtain a high purified virus solution. At the time of performing the test, bovine serum albumin (BSA) was added as a stabilizer to stabilize the viruses.

The virus inactivation action against the influenza virus was confirmed by the method shown in FIG. 1 in the same manner as that of Example 1. Material-carrying samples were prepared in the same manner as that of Example 1. Evaluation was performed as follows. Filter paper was placed in a deep petri dish, and a small volume of sterilized water was added. A glass stand of about 5 mm was placed on the filter paper, and a glass plate (2.5 cm square) applied with a material such as $Cu_2O$ was placed on the filter paper. The purified influenza virus solution was added dropwise in a volume of 50 μL onto the glass plate, and an OHP film was put thereon to have the surface of the material surface contact with the viruses. This petri dish was covered with a glass plate, and irradiated with light. Similar measurement sets were prepared in a number of times of scheduled measurement of virus counts, and left standing in a dark place at room temperature, or at a position where illumination was 1000 luxes (measured with an illuminometer TOPCON IM-5) using a 20 W white fluorescent lamp (FL20S•W, Toshiba Lighting & Technology). After a predetermined time passed, virus infection titers of the samples left in the dark place or irradiated with light were measured.

After the light irradiation, the glass plate inoculated with the virus was immersed in 5 mL of a recovery solution (PBS+1% BSA), and shaken at 100 rpm for 10 minutes on a shaking machine to recover the viruses. The recovered influenza viruses were diluted to $10^8$ viruses/mL by 10-fold serial dilution, and used to infect cultured MDCK cells (dog kidney-derived established cell line), and incubation was performed at 37° C. for 5 days under a $CO_2$ concentration of 5%. After the incubation, presence or absence of cytopathic effect (CPE) in the cells was observed, and by calculating 50% cultured cells infection amount according to the Reed-Muench method, virus infection titer per ml ($TCID_{50}$/ml) was obtained.

Figure 4:
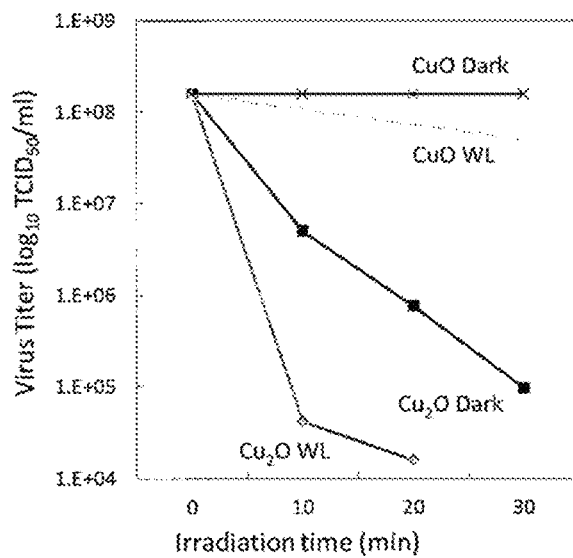
FIG. 4 shows the effect of the agent for virus inactivation of the present invention against influenza virus. In the figure, WL indicates the test results obtained under irradiation of white light, and Dark indicates the test results obtained in a dark place.

The results are shown in FIG. 4. When the influenza viruses were contacted with CuO consisting of a divalent copper ion under the dark condition (Dark), the infection titer did not change after 30 minutes, and inactivation effect was not observed. Similarly, when the viruses were contacted with CuO under the condition of irradiation of light of 1000 luxes with a white fluorescent lamp, almost no decrease in the infection titer was found after 30 minutes, and thus virus inactivation effect was not observed. Whilst, when the influenza viruses were contacted with $Cu_2O$ consisting of a monovalent copper compound under the dark condition (Dark), the infection titer decreased in proportion to the lapsed time, and it decreased to $1/10^3$ after 30 minutes. Similarly, when the viruses were contacted with $Cu_2O$ under the irradiation of light of 1000 luxes with a white fluorescent lamp, the infection titer decreased to $1/10^4$, which was below the detection limit, after 30 minutes. Thus, it was observed that $Cu_2O$ dramatically decreased the infection titer as compared with CuO, and inactivated the influenza viruses under the irradiation of white fluorescence.

Example 4

Figure 5:
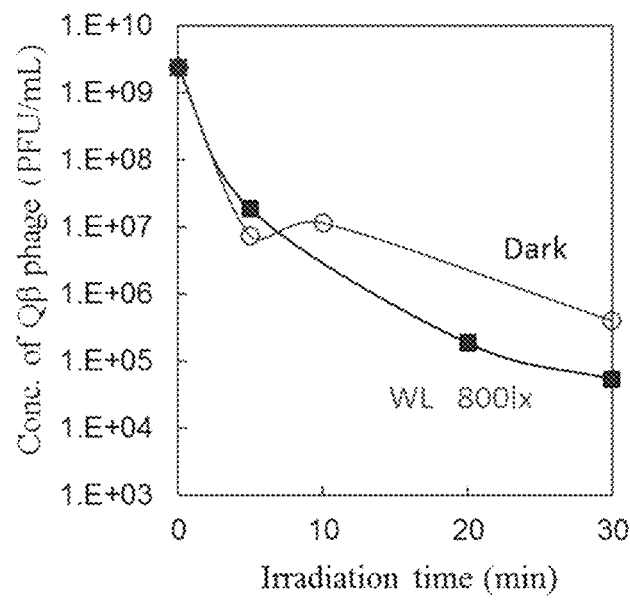
FIG. 5 shows the effect of the agent for virus inactivation of the present invention immobilized on a glass substrate with a binder.

$Cu_2O$ powder was subtilized in a mortar, and added with a hydrolysis solution of TEOS (ethyl silicate 28, Colcoat Co., Ltd.) to prepare an ethanol slurry so that the $Cu_2O$ concentration was 0.1 mass %, and the solid content was 0.1%. When the slurry was prepared, the powder particles were dispersed by irradiating ultrasonic waves for 20 minutes with an ultrasonic washing machine. This dispersion was added dropwise onto whole surface of a glass plate of 2.5 cm×2.5 cm×1 mm (thickness) while avoiding overflow of the dispersion from the glass plate in the same manner as that of Example 1, and this glass plate was put into a constant temperature dryer set at 120° C., and dried for 3 hours. $Cu_2O$ was obtained on the glass plate in an amount of 0.15 mg/6.25 cm$^2$ (=0.24 g/m$^2$). When the phage suspension was contacted for 30 minutes in the same manner as that of Example 1, the phage concentration markedly decreased, and thus it was confirmed that the same phage inactivation activity as that observed in Example 1 was successfully obtained even when a binder was used (FIG. 5).

Example 5

Figure 6:
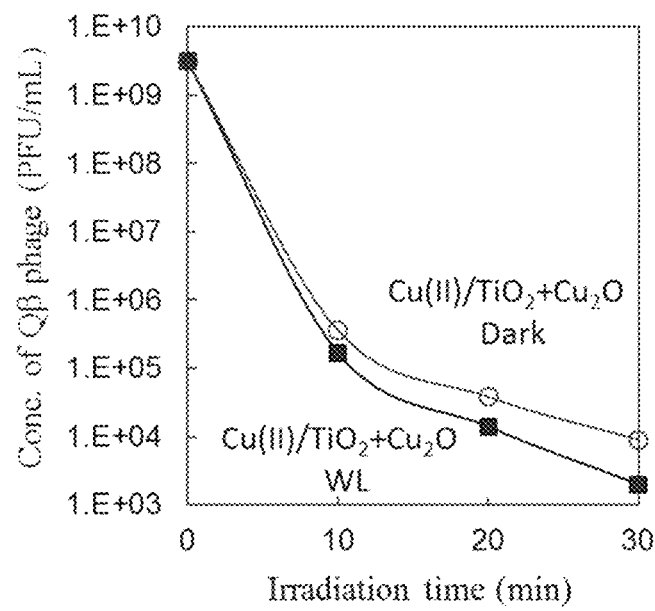
FIG. 6 shows the effect of the agent for virus inactivation in the form of a composition containing cuprous oxide and a photocatalytic substance.

Cu(II)/$TiO_2$ and $Cu_2O$ powders were subtilized in a mortar, and a 0.9 mass % ethanol slurry was prepared. When the slurry was prepared, the powder particles were dispersed by irradiating ultrasonic waves for 20 minutes with an ultrasonic washing machine. This dispersion was added dropwise onto whole surface of a glass plate of 2.5 cm×2.5 cm×1 mm (thickness) in the same manner as that of Example 1 while avoiding overflow of the dispersion from the glass plate, and this glass plate was put into a constant temperature dryer set at 120° C., and dried for 3 hours. Cu(II)/$TiO_2$ and $Cu_2O$ were obtained on the glass plate in amounts of 2.5 mg/6.25 cm$^2$ (=4 g/m$^2$) and 0.15 mg/6.25 cm$^2$ (=0.24 g/m$^2$), respectively. When the phage suspension was contacted for 30 minutes in the same manner as that of Example 1, the phage concentration markedly decreased, and thus it was confirmed that the same phage inactivation activity as that observed in Example 1 was successfully obtained even with a composition containing $Cu_2O$ and a photocatalytic substance (FIG. 6).

Example 6

Figure 8:
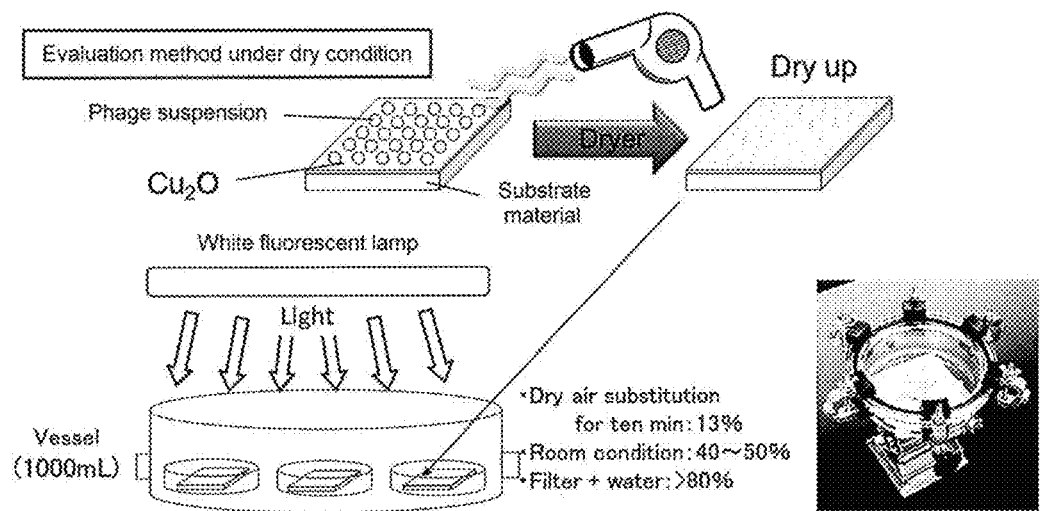
FIG. 8 shows a method for evaluating virus inactivation action in a dry state.
Figure 9:
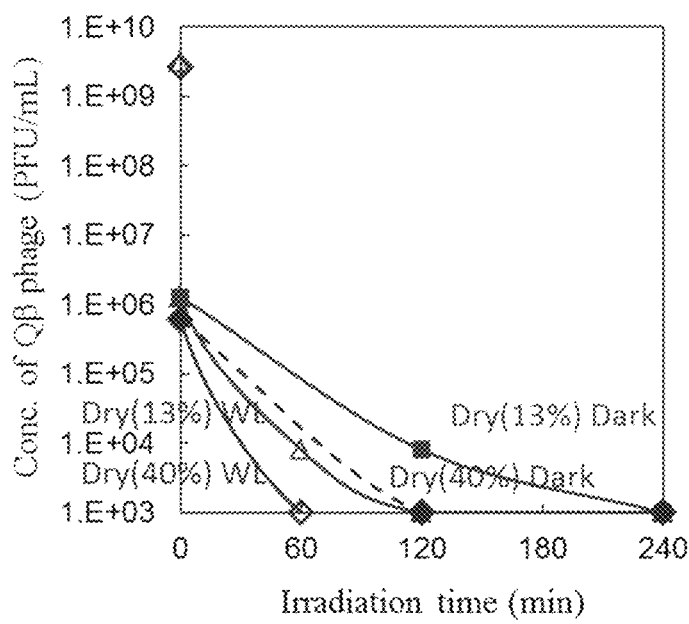
FIG. 9 shows the effect of the agent for virus inactivation of the present invention in a dry state.
Figure 10:
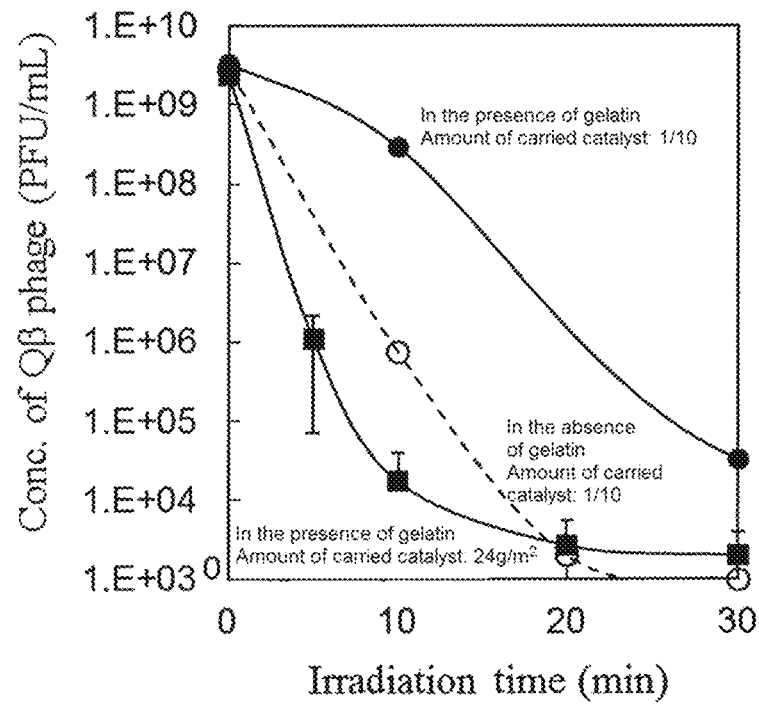
FIG. 10 shows the effect of the agent for virus inactivation of the present invention on a sample containing gelatin as an organic substance.

The evaluation of the virus inactivation action performed in Example 1 and the like utilized the evaluation system comprising filter paper containing water, and accordingly, the humidity at the time of the evaluation was about 80% or higher. It is known that activity of viruses generally becomes low at high humidity, and the activity becomes high at low humidity. Therefore, it was studied whether the agent for virus inactivation of the present invention successfully maintains the high activity even under low humidity conditions. A conceptual diagram of the evaluation method is shown in FIG. 8. When the evaluation was performed with a carried $Cu_2O$ amount corresponding to ⅓ of that used in Example 1 (0.08 g/m$^2$) under a humidity condition of 40% or 13%, the phage concentration decreased to $1/10^3$ at the time of drying, then the phage concentration was successfully decreased to a level below the detection limit with light irradiation only for 1 hour at 40% humidity, and the phage concentration was decreased to a level below the detection limit by contact with $Cu_2O$ only for 4 hours even under the dark place condition at 13% humidity (FIG. 9). These results indicate that $Cu_2O$ can exhibit sufficient virus inactivation effect in a common life space in winter and the like Example 7

Since viruses existing in common life spaces coexist with various organic substances such as dust, it was examined whether the agent for virus inactivation of the present invention successfully exhibits sufficient inactivation action even in the presence of an organic substance. A phage suspension containing 0.1% of gelatin was prepared, and used to perform the evaluation in the same manner as that of Example 1. It was found that, when the amount of carried $Cu_2O$ was 0.24 g/m$^2$, virus inactivation action was promptly exhibited against the sample containing 0.1% of gelatin. Whilst, when the amount of carried $Cu_2O$ was decreased to 1/10, the inactivation action was achieved at a comparable level against a sample not containing gelatin, and thus it was suggested that presence of an organic substance might affect the virus inactivation ability.

Example 8

Figure 11:
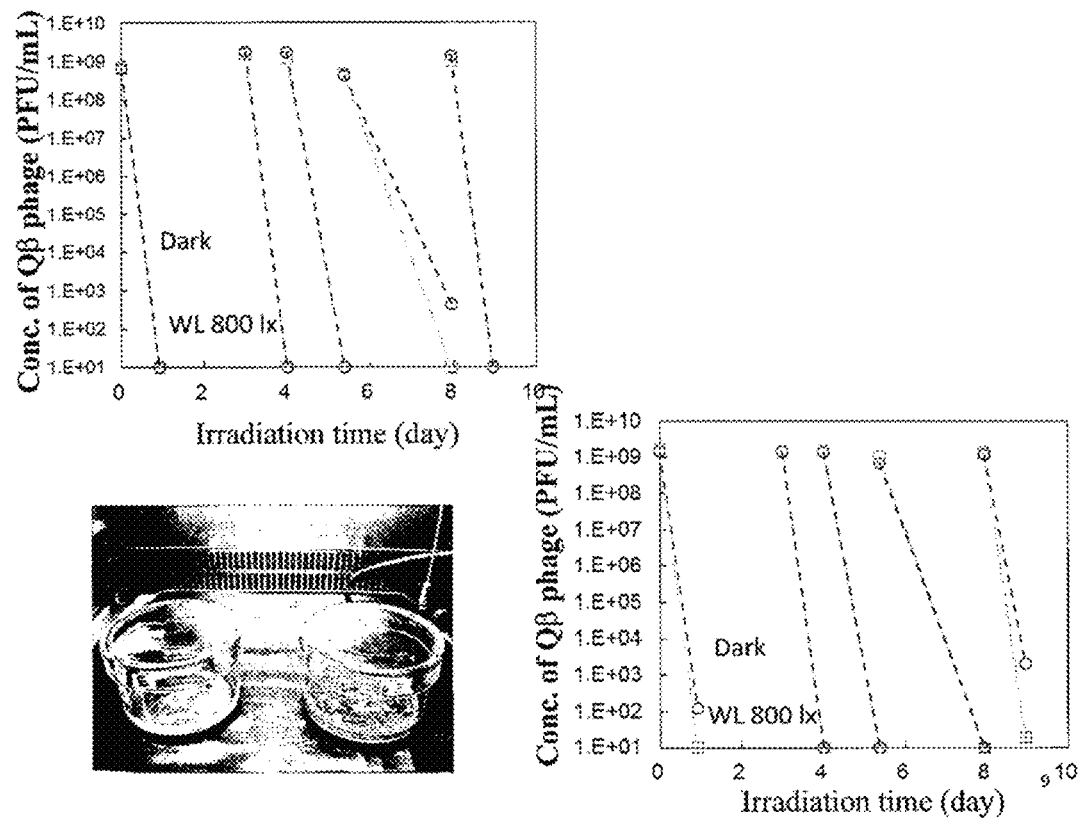
FIG. 11 shows that the agent for virus inactivation of the present invention exhibits persistent virus inactivation action when it is repeatedly exposed to viruses in water. In the figure, the upper left graph shows the results obtained with $Cu_2O$ shirasu balloon, and the lower right graph shows the results obtained with $Cu_2O$ powder.

As shown in FIG. 11, 25 mL of a phage solution in which phages were suspended in the 1/500 NB medium, and $Cu_2O$-coated shirasu balloon (left side in the photograph shown on the lower left side of the figure, 3 g $Cu_2O$/25 mL (1/500NB medium)) or $Cu_2O$ powder (right side in the photograph shown on the lower left side of the figure, 4 mg $Cu_2O$/25 mL (1/500 NB medium)) were put into a high-wall petri dish, and irradiated with light from a white fluorescent lamp (WL) from above. The same experiment system was also placed in a dark place. After about 24 hours, the phage solution was sampled, and phage concentration was determined. As a result, the phage concentration decreased to a level below the detection limit in both of the phage solutions placed under irradiation of white light (WL) and in the dark place. After the sampling, phages were added again, the phage solution was sampled after about 24 hours, and the phage concentration was determined in a similar manner. As a result, the phage concentration was below the detection limit. When this operation was repeated further 5 times, the inactivation effect was observed after each of 5 times of the operation, and thus it was revealed that the virus inactivation action was sustained even after the material was repeatedly exposed to viruses in water (FIG. 11, upper left, $Cu_2O$ shirasu balloon; lower right, $Cu_2O$ powder).

Example 9

Figure 12:
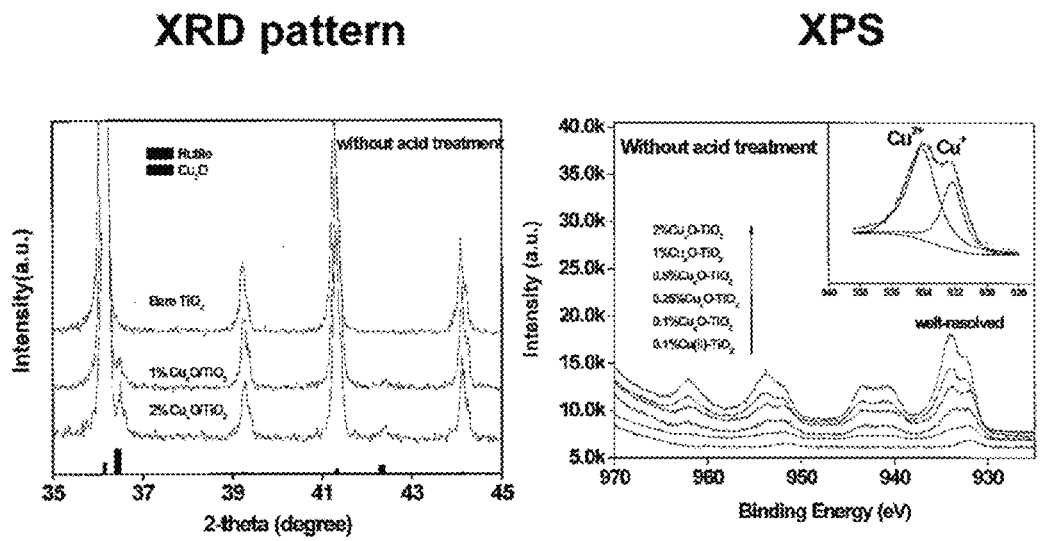
FIG. 12 shows the X-ray diffraction (XRD) patterns and XPS (X-ray photoelectron spectroscopy) spectra of the particles obtained in Example 9.
Figure 13:
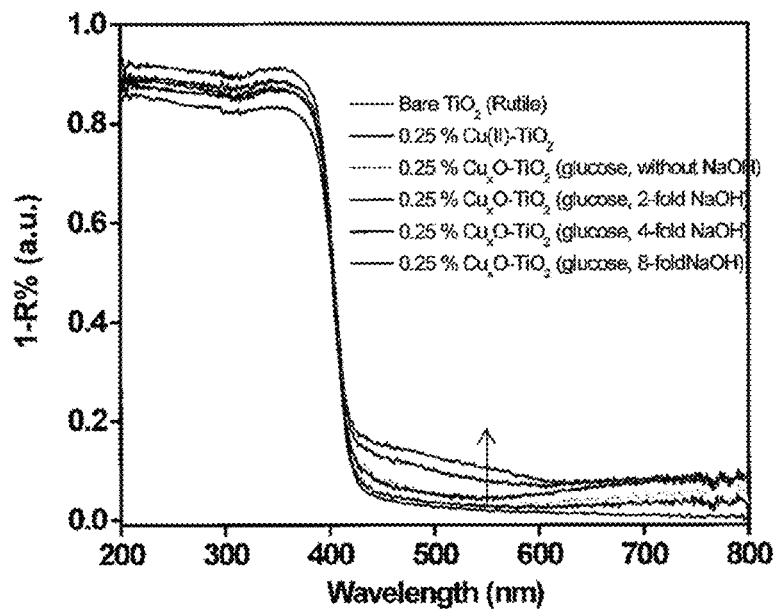
FIG. 13 shows ultraviolet and visible absorption spectra of the composite particles obtained in Example 9.

A suspension was prepared by suspending $TiO_2$ (1.0 g) in a $CuCl_2$ solution (10 ml, 0.1 to 2 wt %) and stirring the mixture at 90° C. for 1 hour. The resulting suspension was added with sodium hydroxide so that the molar ratio of sodium hydroxide to copper ions (NaOH/$Cu^{2+}$) became 0 to 8, and further added with glucose as a reducing substance so that the molar ratio of glucose to copper ions (glucose/$Cu^{2+}$) became 4, and the mixture was further stirred at 90° C. for 1 hour. The resulting solid was collected by filtration, washed with water, and dried to obtain $Cu_xO$—$TiO_2$. The $Cu_xO$—$TiO_2$ obtained by this reaction was composite particles carrying nanoclusters of $Cu_xO$, containing $Cu_2O$ generated by the reaction represented as R—CHO+$2Cu^{2+}$+$4OH^-$->R—COOH+$Cu_2O$+$2H_2O$ (mixture of monovalent and divalent copper oxides) as the component, on the surfaces of $TiO_2$ particles. The X-ray diffraction (XRD) patterns and XPS (X-ray photoelectron spectroscopy) spectra of the resulting particles are shown in FIG. 12. Ultraviolet and visible absorption spectra of the composite particles are shown in FIG. 13. It was observed that absorption due to $Cu_2O$ increased as the amount of NaOH increased. On the basis of these results, it was found that the copper compound carried on the surfaces of the aforementioned particles consisted of a mixture of divalent copper oxide and monovalent copper oxide.

Figure 14:
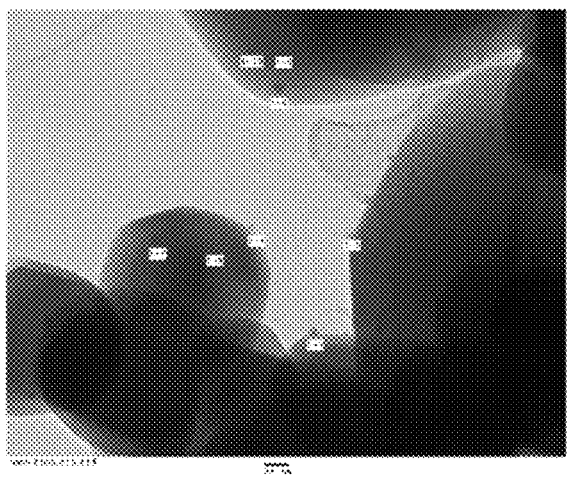
FIG. 14 shows a transmission electron microscopic image and the results of composition analysis with an energy dispersive X-ray (EDX) spectrometer of the composite particles obtained in Example 9.
Figure 14:
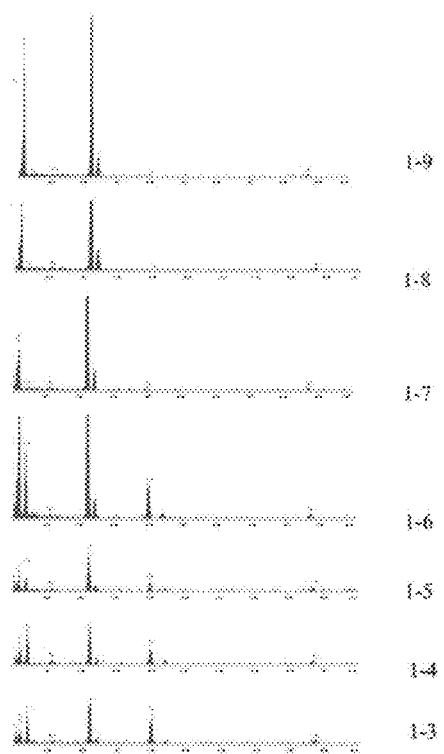

The result of observation of the composite particles with a transmission electron microscope (TEM) is shown in FIG. 14. On the basis of this result, it was revealed that microparticles in the form of nanoclusters having a particle size of about 5 nm were formed and carried on the titanium oxide surfaces. When the particles in the shape of nanoclusters were analyzed with an energy dispersive X-ray spectrometer (EDX), copper was detected only from the positions of the particles in the form of nanoclusters. Also on the basis of these results, it was revealed that the microparticles in the form of nanoclusters were microparticles consisting of copper compounds.

Figure 15:
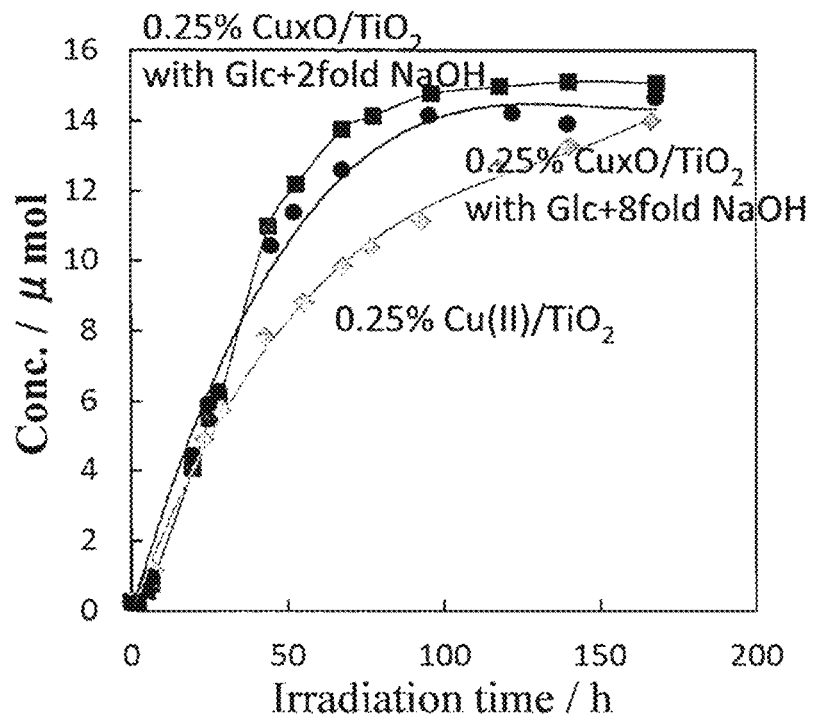
FIG. 15 shows the results of observation of 2-propanol (IPA) decomposition action of the composite particle obtained in Example 9 under irradiation of visible light.

The decomposition action of the resulting particles on 2-propanol (IPA) was studied with visible light. A powder sample (300 mg) contained in a petri dish of 5.5 $cm^2$ was left standing in a 500-mL volume Pyrex glass vessel, the air in the vessel was replaced with pure air, then 6 μmol of 2-propanol was put into the dish, left standing for 12 hours in a dark place, and irradiated with light from a xenon light source (400 to 530 nm), and generated $CO_2$ amount was quantified by gas chromatography. The resulting results are shown in FIG. 15. The composite particles prepared by using glucose showed higher activity compared with Cu(II)/$TiO_2$. The amount of sodium hydroxide used for the preparation of the composite particles did not significantly affect the activity.

Figure 16:
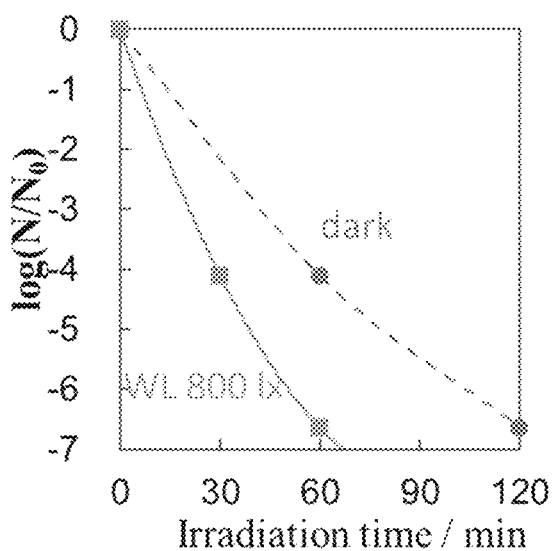
FIG. 16 shows the result of evaluation of virus inactivation action of the composite particles obtained in Example 9 (composite particles, 0.25% $Cu_xO/TiO_2$ glucose+8-fold volume of NaOH)

A sample was prepared by using the resulting particles in the same manner as that of Example 1, and used for evaluation of the virus inactivation action. The composite particles, which was prepared with glucose in an amount 4 times as much as the copper amount and sodium hydroxide in an amount 8 times as much as the copper amount, inactivated the viruses to a level below the detection limit both in the dark place and under the white light irradiation, and thus exhibited marked virus inactivation action (FIG. 16). On the basis of the above results, it is clearly understood that the resulting composite microparticles can be used as a material that successfully exhibit light-induced decomposition activity as well as marked virus inactivation activity.

What is claimed is:

1. A method for inactivating a virus comprising contacting the virus in a dark place with a $TiO_2$ particle that carries on its surface a nanocluster of a mixture containing a monovalent copper oxide and a divalent copper oxide, wherein contact of the virus with the particle in the dark results in virus inactivation under dark conditions.

2. The method for inactivating a virus according to claim 1, wherein the monovalent copper compound is in the form of microparticles.

3. The method for inactivating a virus according to claim 1, comprising contacting the virus with the $TiO_2$ particle and at least one other visible-light-responsive photocatalytic substance.

4. The method for inactivating a virus according to claim 1, wherein the $TiO_2$ particle is on a surface and/or inside of a substrate.

5. The method for inactivating a virus according to claim 4, wherein the $TiO_2$ particle is on the surface of the substrate and immobilized using a binder.

6. The method for inactivating a virus according to claim 4, wherein a dispersion comprising the $TiO_2$ particle dispersed in a resin is coated on the surface of the substrate and is cured.

7. The method according to claim 3, wherein the at least one other visible-light-responsive photocatalytic substance is tungstic oxide.

8. The method according to claim 1, wherein the dark place is the inside of a machine.

9. The method according to claim 1, wherein the dark place is the inside of a refrigerator.

10. The method according to claim 1, wherein the dark place is a darkened room.

11. The method according to claim 10, wherein the dark place is a darkened hospital room.

12. The method according to claim 11, wherein the dark place is a darkened hospital waiting room.

13. The method according to claim 11, wherein the dark place is a darkened hospital operating room.

* * * * *

UNITED STATES PATENT AND TRADEMARK OFFICE
CERTIFICATE OF CORRECTION

PATENT NO. : 9,572,347 B2
APPLICATION NO. : 13/994406
DATED : February 21, 2017
INVENTOR(S) : Kazuhito Hashimoto et al.

It is certified that error appears in the above-identified patent and that said Letters Patent is hereby corrected as shown below:

Foreign Application Priority Data (30) please delete "Dec. 24, 2009 (JP) 2009-292258".

Signed and Sealed this
Fourth Day of July, 2017

Joseph Matal
*Performing the Functions and Duties of the*
*Under Secretary of Commerce for Intellectual Property and*
*Director of the United States Patent and Trademark Office*